United States Patent [19]

Groenenboom et al.

[11] 4,234,501
[45] Nov. 18, 1980

[54] PROCESS FOR THE PREPARATION OF ORGANOTIN COMPOUNDS

[75] Inventors: Cornelis J. Groenenboom, Arnhem; Willem G. B. Huysmans, Ellecom, both of Netherlands; Joseph W. Burley, Warrington, England; Ronald E. Hutton, Southport, England; Michael R. J. Jolley, Skelmersdale, England

[73] Assignee: Akzo N.V., Arnhem, Netherlands

[21] Appl. No.: 958,877

[22] Filed: Nov. 8, 1978

[30] Foreign Application Priority Data

Nov. 9, 1977 [NL] Netherlands .......................... 7712313

[51] Int. Cl.$^3$ .............................................. C07F 7/22
[52] U.S. Cl. ................................................ 260/429.7
[58] Field of Search ..................................... 260/429.7

[56] References Cited

U.S. PATENT DOCUMENTS

| | | | |
|---|---|---|---|
| 3,085,102 | 4/1963 | Yatagai et al. | 260/429.7 |
| 3,332,970 | 7/1967 | Smith | 260/429.7 |
| 3,404,167 | 10/1968 | Gray et al. | 260/429.7 |
| 3,414,595 | 12/1968 | Oakes | 260/429.7 |
| 3,415,857 | 12/1968 | Hoye | 260/429.7 |
| 3,440,255 | 4/1969 | Matsuda et al. | 260/429.7 |
| 3,475,472 | 10/1969 | Suzuki et al. | 260/429.7 |
| 3,475,473 | 10/1969 | Tahara et al. | 260/429.7 |
| 3,547,965 | 12/1970 | Takubo et al. | 260/429.7 |
| 3,651,108 | 3/1972 | Massimo et al. | 260/429.7 |
| 4,105,684 | 8/1978 | Hutton et al. | 260/429.7 |

OTHER PUBLICATIONS

J. Appl. Chem. 9 (1959).
J. Appl. Chem. 11 38-40 (1961).
Sisido et al., J. Organometal. Chem. 9, pp. 99–107, (1967).
Sisido et al., J. Organometal. Chem. 11, pp. 503–513 (1968).

Primary Examiner—Helen M. S. Sneed
Attorney, Agent, or Firm—Stevens, Davis, Miller & Mosher

[57] ABSTRACT

Organotin compounds having the formula $R_3SnX$ or $R_4Sn$ are prepared by reacting metallic zinc with organotin compounds having the formula $RSnX_3$ or $R_2SnX_2$, wherein X stands for chlorine, bromine, iodine or an alkyl carboxylate group having the formula $C_pH_{2p+1}COO$, wherein p=1–18, and R represents an organic group.

Satisfactory yields are obtained under mild reaction conditions and without any catalyst being needed if both in the reacting organotin compounds and in the organotin compounds obtained the group R has the structure

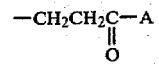

with A being selected from the group consisting of alkyl having 1–18 carbon atoms, O-alkyl having 1–18 carbon atoms and optionally carrying an alkoxy group having 1–18 carbon atoms, polyoxyalkylene consisting of oxyalkylene groups having 1–4 carbon atoms and carrying as terminal group alkyl or a hydrogen atom, O-cycloalkyl, O-alkenyl having 2–4 carbon atoms, O-phenyl, $NH_2$ and alkyl substituted amino, and Cl.

3 Claims, No Drawings

PROCESS FOR THE PREPARATION OF ORGANOTIN COMPOUNDS

The invention relates to a process of preparing organotin compounds having the formula $R_{4-n}SnX_n$, wherein $n=0$ or $1$, by reacting metallic zinc with organotin compounds having the formula $R_{4-m}SnX_m$, wherein $m=2$ or $3$, and X stands for chlorine, bromine, iodine or an alkyl carboxylate group having the formula $C_pH_{2p+1}COO$, wherein $p=1-18$, and R represents an organic group.

A process of the type indicated is described in J. Organometal. Chem. 11 (1968), p. 503–513. The process of the type indicated above particularly relates to the conversion of dialkyltin dichloride into trialkyltin chloride and tetraalkyltin in the presence of certain metals, such as zinc. The reported yields of these conversions, if any, are generally low. Moreover, the conversions require a high reaction temperature (160° C., autoclave) and in the case of a non-aqueous reaction medium the presence of an organic base, like triethylamine or pyridine, as catalyst.

It is an object of this invention to provide a process for the preparation of organotin compounds giving satisfactory yields under mild reaction conditions and without any catalyst being needed. The objects of the present invention are accomplished if the conversion is carried out with organotin compounds of a specific composition.

According to the invention both in the reacting organotin compounds and in the organotin compounds obtained the organic group R has the structure

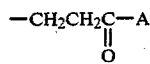

with A being selected from the group consisting of alkyl having 1–18 carbon atoms, O-alkyl having 1–18 carbon atoms and optionally carrying an alkoxy group having 1–18 carbon atoms, polyoxyalkylene consisting of oxyalkylene groups having 1–4 carbon atoms and carrying as terminal group alkyl or a hydrogen atom, O-cycloalkyl, O-alkenyl, having 2–4 carbon atoms, O-phenyl, $NH_2$ and alkyl substituted amino, and Cl.

Examples of alkyl having 1–18 carbon atoms are methyl, ethyl, propyl, butyl, pentyl, hexyl, heptyl, octyl, 2-ethyl hexyl, nonyl, decyl, dodecyl and octadecyl. Examples of O-alkyl having 1–18 carbon atoms are methoxy, ethoxy, propoxy, n-butoxy, and octadecyloxy. Examples of polyoxyalkylene consisting of oxyalkylene groups having 1–4 carbon atoms and carrying as terminal group alkyl or a hydrogen atom are ethoxyethyloxy and n-butoxyethyloxyethyloxy. An example of O-cycloalkyl is O-cyclohexyl. An example of O-alkenyl having 2–4 carbon atoms in allyloxy. Examples of alkyl substituted amino are N-methylamino and N,N-dimethylamino. The organotin compounds of formula $R_{4-m}SnX_m$ with $m=2$ or $3$ and wherein R and X are as defined above are of a type generally known in the art.

Thus the compounds $RSnX_3$ and a useful method for their preparation are for instance described in U.S. Pat. No. 4,105,684.

Similarly, the compounds $R_2SnX_2$ and their preparation are described in British Patent Specification No. 1 502 073. Quite unexpectedly and in contrast to the mono- and dialkyltin compounds these known compounds, wherein R has the structure as defined above, can be easily converted with metallic zinc into the corresponding compounds $R_3SnX$ and $R_4Sn$.

Although the invention generally contemplates the conversion of either $RSnX_3$ or $R_2SnX_2$ into $R_3SnX$ and/or $R_4Sn$, it has further been found that certain preferred embodiments are applicable.

Thus, in preparing $R_3SnX$ from the corresponding $RSnX_3$ it is preferred to react the latter with metallic zinc in an organic solvent medium and at a temperature not exceeding about 35° C. If on the other hand one wishes to convert $R_2SnX_2$ into the corresponding $R_3SnX$ it is advisable that the reaction be carried out with metallic zinc in an organic solvent medium at a temperature above about 35° C. Conveniently, in this case an organic solvent having an atmospheric boiling point above about 35° C. is employed and the reaction carried out at the atmospheric reflux temperature of the solvent medium.

Finally, when it is desired to prepare the compound $R_4Sn$ this can suitably be achieved by continuing reacting $R_2SnX_2$ with metallic zinc under the foregoing conditions for a sufficient length of time.

By properly selecting the period over which the reaction with zinc is allowed to proceed it is possible to obtain either predominantly $R_3SnX$ or $R_4Sn$. Of course, at intermediate reaction times a mixture of the conversion products is obtained which may subsequently be separated. Similarly, the compound $RSnCl_3$ may be converted into $R_4Sn$.

The conversion products obtained by the process of this invention are of potential interest for their biological activities.

The antifungal properties of a number of functionally substituted organotin compounds have been reported in J. Appl. Chem. 11, 38–40 (1961).

Specifically, one compound of subject type $R_3SnX$ has been so reported therein, namely tri-(2-methoxycarbonylethyl)tin bromide. Compounds of subject type $R_4Sn$ are disclosed in U.S. Pat. No. 3,332,970.

By way of illustration various embodiments of the invention are presented in the following examples.

CONVERSION OF $RSnX_3$ INTO $R_3SnX$

EXAMPLE I 60 g of 2-methoxycarbonylethyltin trichloride $Cl_3SnCH_2CH_2COOCH_3$ were dissolved in 300 ml of diethyl ether. 33 g of zinc powder were then added and the mixture was stirred at room temperature for 20 hours. The reaction mixture was filtered and the residue washed with dimethoxyethane. The combined filtrates were treated with gaseous HCl and then washed with dilute hydrochloric acid and water, in that order.

The organic phase was dried over anhydrous sodium sulphate and the solvent was then removed on a thin-film evaporator to leave 19.4 g of a colourless oil, identified as tri(2-methoxycarbonylethyl)tin chloride, $ClSn(CH_2CH_2COOCH_3)_3$ (yield 73%).

EXAMPLE II

The procedure of Example I was repeated using 60 g of 2-n-butoxycarbonylethyltin trichloride $Cl_3SnCH_2CH_2COOn-C_4H_9$ and 30 g of zinc powder, and the residue of the reaction mixture was washed with diethyl ether instead of dimethoxyethane. After final evaporation of the solvent there were obtained 23.3 g of a pale yellow oil, identified as tri(2-n-butoxycarbonylethyl)tin chloride, ClSn(CH$_2$CH$_2$COOn-C$_4$H$_9$)$_3$ (yield 75%).

EXAMPLE III 5 g of 2-methoxycarbonylethyltin tribromide Br$_3$SnCH$_2$CH$_2$COOCH$_3$ were dissolved in 50 ml of toluene, and 2 g of zinc powder were added. The mixture was heated under reflux for 5 hours, with rapid stirring. The mixture was filtered and the residue washed with dimethoxyethane. The combined filtrates were treated with gaseous HBr, then washed with dilute hydrobromic acid and water and finally dried over magnesium sulphate. The solvent was then removed on a thin-film evaporator to leave 1.0 g of a yellow oil, identified as tri(2-methoxycarbonylethyl)tin bromide, BrSn(CH$_2$CH$_2$COOCH$_3$)$_3$ (yield 58%).

EXAMPLE IV 10 g of 2-phenoxycarbonylethyltin trichloride Cl$_3$SnCH$_2$CH$_2$COOC$_6$H$_5$ were dissolved in 100 ml of toluene, and 4 g of zinc powder were added. The mixture was heated under reflux for 12 hours, with rapid stirring. The mixture was filtered and the residue washed with dimethoxyethane. The combined filtrates were treated with gaseous HCl, then successively washed with dilute hydrochloric acid and water and then dried over magnesium sulphate. The solvent was then removed on a thin-film evaporator to leave 2.5 g of a yellow oil, identified as tri(phenoxycarbonylethyl)tin chloride, ClSn(CH$_2$CH$_2$COOC$_6$H$_5$)$_3$ (yield 47%).

EXAMPLE V 5 g of 2-ethoxyethyloxycarbonylethyltin trichloride Cl$_3$Sn(CH$_2$CH$_2$COOCH$_2$CH$_2$OCH$_2$CH$_3$) dissolved in 50 ml of toluene and 2 g of zinc powder were added. The mixture was heated under reflux for 1.5 hours, with rapid stirring. The mixture was cooled and filtered. The residue was washed with dimethoxyethane. The combined filtrates were treated with gaseous HCl and successively washed with dilute hydrochloric acid and water. They were dried over magnesium sulphate and the solvent was then removed on a thin-film evaporator to leave 1.1 g of a pale yellow oil, identified as tri(2-ethoxyethyloxycarbonylethyl)tin chloride, ClSn(CH$_2$CH$_2$COOCH$_2$CH$_2$OCH$_2$CH$_3$)$_3$ (yield 41.5%).

CONVERSION OF R$_2$SnX$_2$ INTO R$_3$SnX

EXAMPLE VI 200 g of di(2-n-butoxycarbonylethyl)tin dichloride Cl$_2$Sn(CH$_2$CH$_2$COOn-C$_4$H$_9$)$_2$ were dissolved in one liter of diethyl ether, and 30 g of zinc powder were added. The mixture was heated under reflux with rapid stirring for 21 hours. The reaction mixture was then cooled and filtered and the residue washed with dimethoxyethane. The combined filtrates were treated with gaseous HCl, then washed with dilute hydrochloric acid and water and finally dried over magnesium sulphate. The solvent was then removed on a thin-film evaporator to leave 134.2 g of a pale yellow oil, identified as tri(2-n-butoxycarbonylethyl)tin chloride, ClSn(CH$_2$CH$_2$COOn-C$_4$H$_9$)$_3$ (yield 83.2%).

EXAMPLE VII

The procedure of Example VI was repeated using 100 ml of toluene as solvent medium in which 10 g of the same organotin dichloride were reacted with 2 g of zinc powder under reflux conditions for 2 hours. After final evaporation of the solvent there were obtained 7.1 g of the corresponding organotin monochloride (yield 88%).

EXAMPLE VIII

In this experiment 30 g of di(2-phenoxycarbonylethyl)tin dichloride Cl$_2$Sn(CH$_2$CH$_2$COOC$_6$H$_5$)$_2$ and 4 g of zinc powder were reacted in 200 ml toluene under reflux for 20 hours. Using the same procedure as before there were finally obtained 15.2 g of a yellow oil, identified as tri(2-phenoxycarbonylethyl)tin chloride (yield 61.6%).

EXAMPLE IX

Using the same procedure as before 10 g of di(2-n-butoxycarbonylethyl)tin dibromide and 2 g of zinc powder were reacted in 100 ml of toluene under reflux for 5 hours. In this case the combined filtrates were treated with gaseous HBr, followed by successively washing with dilute hydrobromic acid and water. Removal of the solvent by evaporation finally yielded 5.2 g of a pale yellow oil, identified as tri(2-n-butoxy-carbonylethyl)tin bromide (yield 71.4%).

EXAMPLE X

In this experiment no solvent medium was used. 20 g of the same organotin dichloride as in Example VI were reacted with 4 g of zinc powder by simply stirring together at 100° C. for 20 hours.

The reaction mixture was cooled, then diluted with dimethoxyethane and further processed as described before. Upon evaporation of the organic diluent there were obtained 6.2 g of a pale yellow oil, identified as before (yield 76.9%).

EXAMPLE XI 2 g of di(2-methylcarbonylethyl)tin dichloride Cl$_2$Sn(CH$_2$CH$_2$COCH$_3$)$_2$ were dissolved in a mixture of 20 ml of diethyl ether and 10 ml of tetrahydrofuran. After the addition of 2 g of zinc powder the mixture was heated under reflux for 40 hours, with rapid stirring. The reaction mixture was then further processed as in Example VI. Solvent removal yielded 1.1 g of a pale yellow oil, identified as tri(2-methylcarbonylethyl)tin chloride, ClSn(CH$_2$CH$_2$COCH$_3$)$_3$ (yield 74.5%).

EXAMPLE XII 3.2 g of di(2-ethylcarbonamide)tin dichloride Cl$_2$Sn(CH$_2$CH$_2$CONH$_2$)$_2$ were dissolved in 40 ml of tetrahydrofuran and reacted with 10 g of zinc powder while heating the mixture under reflux for 20 hours with rapid stirring. The reaction mixture was otherwise processed as in Example VI, which resulted in 1.6 g of a pale yellow oil, identified as tri(2-ethylcarbonamide)tin chloride, ClSn(CH$_2$CH$_2$CONH$_2$)$_3$ (yield 67%).

EXAMPLE XIII 2 g of di(2-octadecyloxycarbonylethyl)tin dichloride Cl$_2$Sn(CH$_2$CH$_2$COOC$_{18}$H$_{37}$)$_2$ were dissolved in 20 ml of toluene, and 0.5 g of zinc powder were added. The mixture was heated under reflux for 50 hours, with rapid stirring. The mixture was cooled and filtered. The residue was washed with dimethoxyethane and the combined filtrates were treated with gaseous HCl and then successively washed with dilute hydrochloric acid and water. They were dried over magnesium sulphate and the solvent was removed on a thin-film evaporator. The resulting oil crystallised to give an off white solid 1.7 g m.p. 57°–59° C., which was identified as tri(2-octadecyloxycarbonylethyl)tin chloride, $ClSn(CH_2CH_2COOC_{18}H_{37})_3$ (yield 95%).

EXAMPLE XIV 5 g of di(2-n-butoxyethyloxyethyloxycarbonylethyl)-tin dichloride $Cl_2Sn(CH_2CH_2COOCH_2CH_2OCH_2CH_2On-C_4H_9)_2$ were dissolved in 50 ml of toluene and 1 g of zinc powder was added. The mixture was heated under reflux with rapid stirring for 1.5 hours and then cooled. It was filtered and the residue washed with dimethoxyethane and the combined filtrates were treated with gaseous HCl and successively washed with dilute hydrochloric acid and water. The organic layer was dried over magnesium sulphate and the solvent removed on a thin-film evaporator to leave 3.2 g of a pale yellow oil which was identified as tri(2-butoxyethyloxyethyloxycarbonylethyl)tin chloride, $ClSn(CH_2CH_2COOCH_2CH_2OCH_2CH_2On-C_4H_9)_3$ (yield 74.4%).

EXAMPLE XV 10 g of di(2-cyclohexyloxycarbonylethyl)tin dichloride and 2 g of zinc powder were reacted in 100 ml of toluene under reflux for 7 hours with rapid stirring. The mixture was then cooled, filtered and the residue was washed with dimethoxyethane and the combined filtrates were treated with gaseous HCl and then successively washed with dilute hydrochloric acid and water. The organic phase was dried over magnesium sulphate and the solvent was removed on a thin-film evaporator to leave 5.2 g of a viscous oil, which was identified as tri(2-cyclohexyloxycarbonylethyl)tin chloride, $ClSn(CH_2CH_2COOC_6H_{11})_3$ (yield 63%).

EXAMPLE XVI 10 g of di(2-allyloxycarbonylethyl)tin dichloride and 2 g of zinc powder were reacted in 100 ml of toluene for 2 hours at reflux with stirring. The reaction mixture was then processed as in Example XV to yield 6.2 g of a pale yellow oil, identified as tri(2-allyloxycarbonylethyl)tin chloride, $ClSn(CH_2CH_2COOCH_2CH=CH_2)_3$ (yield 78%).

EXAMPLE XVII 5 g of di(2-N-methyl-ethylcarbonamide)tin dichloride and 2 g of zinc powder were reacted in toluene under reflux for 10 hours with rapid stirring. The reaction mixture was processed as in Example XV to yield 3.2 g of a yellow oil, which was identified as tri(2-N-methyl-ethylcarbonamide)tin chloride, $ClSn(CH_2CH_2CONHCH_3)_3$ (yield 84%).

EXAMPLE XVIII 10 g of di(2-N,N-dimethyl-ethylcarbonamide)tin dichloride and 4 g of zinc powder were reacted in toluene under reflux for 10 hours with stirring. The reaction mixture was processed as in Example XV to yield 6.9 g of a yellow oil, identified as tri(2-N,N-dimethylethylcarbonamide)tin chloride, $ClSn(CH_2CH_2CON(CH_3)_2)_3$ (yield 89%).

CONVERSION OF $R_2SnX_2$ INTO $R_4Sn$

EXAMPLE XIX

In accordance with the reaction procedure of Example VI 60 g of the same organotin dichloride were reacted with 12 g of zinc powder in 300 ml of diethyl ether for a prolonged period of 36 hours. The reaction mixture was cooled and filtered and the residue washed with diethyl ether. The combined filtrates were treated and washed as before and finally dried over anhydrous sodium sulphate. Upon removal of the solvent there remained 35 g of a pale yellow oil, identified as a mixture of about 75 wt. % tetra(2-n-butoxycarbonylethyl)-tin and about 25 wt. % of the corresponding triorganotin chloride. The tetraorganotin compound was subsequently separated by dissolving the mixture in 150 ml of diethyl ether, adding 7.5 ml of a 2 molar NaOH solution, stirring for 4 hours and then adding water to effect phase separation. The water layer was extracted with diethyl ether and the combined organic extracts were dried over anhydrous sodium sulphate. The solvent was finally removed on a thin-film evaporator to leave 25 g of a pale yellow oil, identified as pure tetra(2-n-butoxycarbonylethyl)tin, $Sn(CH_2CH_2COOn-C_4H_9)_4$ (yield 58%).

EXAMPLE XX

The procedure of Example XIX was repeated with 60 g of di(2-methoxycarbonylethyl)tin dichloride and 14 g of zinc powder and using dimethoxyethane for washing the residue of the reaction mixture. Upon removal of the solvent there were obtained 28 g of a colourless oil, identified as a mixture of about 70 wt.% of the tetraorganotin compound and about 30 wt.% of the corresponding triorganotin chloride.

Purification was effected as before, using 14 ml of a 2 molar NaOH solution and a stirring time of one hour. Upon removal of the solvent there finally remained 20.6 g of a colourless oil, identified as tetra(2-methoxycarbonylethyl)tin, $Sn(CH_2CH_2COOCH_3)_4$ (yield 45%).

EXAMPLE XXI 10 g of di(2-n-butoxycarbonylethyl)tin diacetate $(CH_3COO)_2Sn(CH_2CH_2COOn-C_4H_9)_2$ were dissolved in 100 ml of toluene and 4 g of zinc powder were added. The mixture was heated under reflux with rapid stirring for 8 hours. The mixture was cooled and filtered. The filtrate was washed with dimethoxyethane and the combined filtrates were treated with water. The mixture was again filtered and the filtrate washed with further amounts of water. The organic phase was dried over magnesium sulphate and the solvent was removed on a thin-film evaporator to leave 5.3 g of a colourless oil identified as tetra (2-n-butoxycarbonylethyl)tin (yield 83%).

EXAMPLE XXII 10 g of di(2-methylcarbonylethyl)tin diacetate were dissolved in 100 ml of tetrahydrofuran and 4 g of zinc powder added. The mixture was heated under reflux with rapid stirring for 20 hours. It was then cooled and filtered. The residue was washed with more tetrahydrofuran and the combined filtrates were treated with diethyl ether and water. The mixture was again filtered and the layers were separated. The organic phase was washed with further amounts of water and then dried over magnesium sulphate and the solvent was removed on a thin-film evaporator to leave 3.9 g of a yellow oil identified as tetra (2-methylcarbonylethyl)tin, $Sn(CH_2CH_2COCH_3)_4$ (yield 73%).

EXAMPLE XXIII 10 g of di(2-ethoxyethyloxycarbonylethyl)tin diacetate were dissolved in 100 ml of toluene and 3 g of zinc powder was added. The mixture was heated under reflux with stirring for 4 hours, cooled and filtered. The filtrate was washed with dimethoxyethane and the combined filtrates were treated with water. The mixture was refiltered and the organic phase was washed with further amounts of water and then dried over magnesium sulphate. Removal of the solvent on a thin-film evaporator gave 4.9 g of a pale yellow oil identified as tetra (2-ethoxyethyloxycarbonylethyl)tin, $Sn(CH_2CH_2COOCH_2CH_2OCH_2CH_3)_4$ (yield 74%).

EXAMPLE XXIV 5 g of di(2-n-butoxyethyloxyethyloxycarbonylethyl)-tin diacetate were dissolved in 50 ml of toluene and 2 g of zinc powder added. The mixture was heated under reflux with stirring for 3 hours, cooled and filtered. The residue was washed with dimethoxyethane and the combined filtrates were treated with water. The mixture was refiltered and the organic phase was washed several times with water and then dried over magnesium sulphate. Removal of the solvent on a thin-film evaporator gave 2.3 g of a yellow oil identified as tetra(2-n-butoxyethyloxyethyloxycarbonylethyl)tin, $Sn(CH_2CH_2COOCH_2CH_2OCH_2CH_2On\text{-}C_4H_9)_4$ (yield 63%).

EXAMPLE XXV 10 g of di(2-cyclohexyloxycarbonylethyl)tin diacetate was dissolved in 100 ml of toluene and 4 g of zinc powder added. The mixture was heated under reflux with rapid stirring for 7 hours, cooled and filtered. The residue was washed with dimethoxyethane and the combined filtrates were treated as in Example XXIII to yield 4.8 g of a pale yellow viscous oil which was identified as tetra(2-cyclohexyloxycarbonylethyl)tin $Sn(CH_2CH_2COOC_6H_{11})_4$ (yield 71%).

EXAMPLE XXVI 10 g of di(2-allyloxycarbonylethyl)tin diacetate was dissolved in 100 ml of toluene and 4 g of zinc powder added. The mixture was heated under reflux with rapid stirring for 6 hours, cooled and filtered. The residue was washed with dimethoxyethane and the combined filtrates were treated as in Example XXIII to yield 5.2 g of a pale yellow oil which was identified as tetra(2-allyloxycarbonylethyl)tin, $Sn(CH_2CH_2COOCH_2CH=CH_2)_4$ (yield 84%).

EXAMPLE XXVII 10 g of di(2-phenoxycarbonylethyl)tin dipropionate was dissolved in 100 ml of toluene and 4 g of zinc powder added. The mixture was heated under reflux with rapid stirring for 16 hours, cooled and filtered. The residue was washed with dimethoxyethane and the combined filtrates were treated as in Example XXIII to yield 3.2 g of a yellow oil which was identified as tetra(2-phenoxycarbonylethyl)tin, $Sn(CH_2CH_2COOC_6H_5)_4$ (yield 50%).

EXAMPLE XXVIII 10 g of di(2-ethylcarbonamide)tin diacetate was dissolved in 100 g of tetrahydrofuran and 6 g of zinc powder added. The mixture was heated under reflux for 20 hours with rapid stirring. The reaction mixture was then processed as in example XXII to give 3.2 g of a pale yellow oil identified as tetra(2-ethylcarbonamide)tin, $Sn(CH_2CH_2CONH_2)_4$ (yield 60%).

EXAMPLE XXIX 5 g of di(2-N-methyl-ethylcarbonamide)tin diacetate and 2 g of zinc powder were reacted in 50 ml of toluene under reflux for 10 hours with rapid stirring, cooled and filtered. It was then processed as in Example XXIII to give 2.1 g of a pale yellow oil identified as tetra(2-N-methyl-ethylcarbonamide)tin, $Sn(CH_2CH_2CONHCH_3)_4$ (yield 74%).

EXAMPLE XXX 5 g of di(2-N,N-dimethyl-ethylcarbonamide)tin diacetate and 2 g of zinc powder were reacted in 50 ml of toluene under reflux for 10 hours with stirring, cooled and filtered. The mixture was then processed as in Example XXIII to give 2.2 g of a pale yellow oil identified as tetra (2-N,N-dimethyl-ethylcarbonamide)tin, $Sn(CH_2CH_2CON(CH_3)_2)_4$ (yield 74%).

EXAMPLE XXXI 10 g of di(2-n-butoxycarbonylethyl)tin dilaurate and 2 g of zinc powder were reacted in 100 ml of toluene under reflux for 10 hours with stirring, cooled and filtered. The mixture was treated with water and refiltered. The organic layer of the filtrate was washed with dilute sodium bicarbonate solution and then water. The organic layer was then dried over magnesium sulphate and the solvent was removed on a thin-film evaporator to give 3.2 g of a colourless oil, identified as tetra(2-n-butoxycarbonylethyl)tin, $Sn(CH_2CH_2COOn\text{-}C_4H_9)_4$ (yield 78%).

EXAMPLE XXXII 10 g of di(2-n-butoxycarbonylethyl)tin distearate and 2 g of zinc powder were reacted in 100 ml of toluene under reflux for 10 hours with stirring, cooled and filtered. The filtrate was then processed as in Example XXXI to give 2.5 g of a colourless oil which was identified as tetra(2-n-butoxycarbonlyethyl)tin, $Sn(CH_2CH_2COOn\text{-}C_4H_9)_4$ (yield 74%).

CONVERSION OF $RSnX_3$ INTO $R_4Sn$

EXAMPLE XXXIII 42 g of 2-methoxycarbonylethyltin trichloride were dissolved in 350 ml of diethyl ether and 26 g of zinc powder were added. The mixture was heated under reflux with rapid stirring for 36 hours. The mixture was filtered and the residue was washed with dimethoxyethane. The combined filtrates were treated with gaseous HCl, then washed with dilute aqueous hydrochloric acid and dried over anhydrous sodium sulphate. The solvent was then removed on a thin film evaporator to leave 12.5 g of a colourless oil, which consisted of a mixture of 75 wt.% tetra (2-methoxycarbonylethyl)tin and 25 wt.% of tri (methoxycarbonylethyl)tin chloride. The tetra organotin compound was subsequently separated in accordance with the procedure of Example XIX, resulting in 9.4 g of a colourless oil, identified as tetra(2-methoxycarbonylethyl)tin (yield 60%).

What is claimed is:

1. Process of preparing organotin compounds having the formula $R_{4-n}SnX_n$, wherein $n = 0$ or 1, by reacting under mild reaction conditions without the need of a catalyst, metallic zinc with organotin compounds having the formula $R_{4-m}SnX_m$, wherein $m=2$ or 3, and X stands for chlorine, bromine, iodine or an alkyl carboxylate group having the formula $C_pH_{2p+1}COO-$, wherein $p=1-18$, and R represents an organic group, characterized in that both in the reacting organotin compounds and in the organotin compound obtained the organic group R has the structure

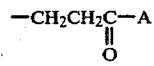

with A being selected from the group consisting of alkyl having 1-18 carbon atoms, O-alkyl having 1-18 carbon atoms and optionally carrying an alkoxy group having 1-18 carbon atoms, polyoxyalkylene consisting of oxalkylene groups having 1-4 carbon atoms and carrying as terminal group alkyl or a hydrogen atom, O-cycloalky, O-alkenyl having 2-4 carbon atoms, O-phenyl, $NH_2$ and alkyl substituted amino, and Cl.

2. Process of preparing organotin compounds of formula $R_3SnX$ according to claim 1, characterized in that organotin compounds of formula $RSnX_3$ are reacted with metallic zinc in an organic solvent medium at a temperature not exceeding about 35° C.

3. Process of preparing organotin compounds of formula $R_3SnX$ and $R_4Sn$ according to claim 1, characterized in that organotin compounds of formula $R_2SnX_2$ are reacted with metallic zinc in an organic solvent medium at a temperature above about 35° C.

* * * * *